United States Patent [19]

Charman et al.

[11] Patent Number: 5,968,987
[45] Date of Patent: Oct. 19, 1999

[54] HALOFANTRINE FREE BASE FOR THE TREATMENT OF MALARIA AND COMPOSITIONS

[75] Inventors: William Neil Charman, Ascot Vale; Christopher John Hamilton Porter, Brunswick, both of Australia

[73] Assignee: Smithkline Beecham p.l.c., Brendford, United Kingdom

[21] Appl. No.: 08/950,459

[22] Filed: Oct. 15, 1997

Related U.S. Application Data

[63] Continuation of application No. 08/718,343, filed as application No. PCT/EP95/01257, Apr. 4, 1995, abandoned.

[30] Foreign Application Priority Data

Apr. 7, 1994 [GB] United Kingdom .................. 9406858
Aug. 13, 1994 [GB] United Kingdom .................. 9416404

[51] Int. Cl.$^6$ ................................. A61K 31/205
[52] U.S. Cl. ................ 514/656; 514/895; 564/370
[58] Field of Search ................. 514/656, 895; 564/370

[56] References Cited

U.S. PATENT DOCUMENTS

| | | | |
|---|---|---|---|
| 4,507,288 | 3/1985 | Rosignol | 514/143 |
| 4,818,767 | 4/1989 | Rossignol | 514/555 |
| 5,278,173 | 1/1994 | Davis | 514/312 |

FOREIGN PATENT DOCUMENTS

WO 93/01809  2/1993  United Kingdom .

OTHER PUBLICATIONS

Nothdurft et al., "Halofantrine: a new substance for treatment of multidrug–resistant malaria", Clincal Investig, 71:69–73, (1993).

Shah et al., "Self–emulsifying drug delivery systems (SEDDS) for improving in vitro dissolution and oral absorption of lipophilic drugs", Bull. Tech/Gattefosse Rep., vol. 85, pp. 45–54, 1993.

*Primary Examiner*—Dwayne C. Jones
*Attorney, Agent, or Firm*—Soma G. Simon; William T. King; Charles M. Kinzig

[57] ABSTRACT

The present invention relates to the use of halofantrine free base in the treatment of malarial infections. In particular, lipid-based formulations for oral and injectable use are disclosed.

8 Claims, 3 Drawing Sheets

HALOFANTRINE FREE BASE FOR THE TREATMENT OF MALARIA AND COMPOSITIONS

This is a continuation of application Ser. No. 08/718,343, filed Oct. 4, 1996 and abandoned on Oct. 16, 1997 which was also a 371 of PCT/EP95/01257, filed Apr. 4, 1995.

The present invention relates to the use of the compound halofantrine in medicine and pharmaceutical formulations containing it.

Halofantrine hydrochloride, that is to say the compound of structure:

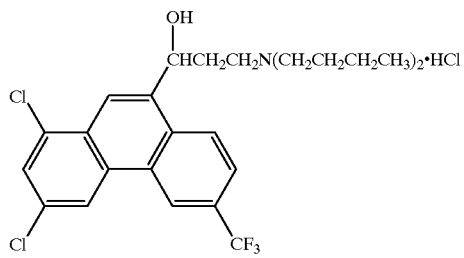

is an anti-malarial compound currently on the market in many countries throughout the world (HALFAN™—Smith Kline & French Laboratories Limited). Whilst the compound has proved very effective in the treatment of malarial infections, its absorption after oral administration is poor and often variable and the resulting erratic plasma profiles may limit therapeutic effectiveness and potentially stimulate the development of resistance. In addition, the poor aqueous and lipid solubility of halofantrine hydrochloride has limited the development of injectable formulations. Injectable formulations can potentially be very valuable for the treatment of severe forms of malaria, in particular cerebral malaria. There therefore exists a strong need for the development of more consistently and effectively absorbed formulations of halofantrine.

It has now been found that the provision of formulations of halofantrine in the form of the free base (as opposed to the hydrochloride salt formulations currently in use) meet this need and provide novel and effective formulations for the treatment of malaria. In particular, the formulations of the present invention comprise the free base form of halofantrine, and it is believed that the disclosure herein is the first disclosure of the use of the free base form in the treatment of malarial infection—all previous reports, and the marketed form use the hydrochloride salt form.

Figure 1:
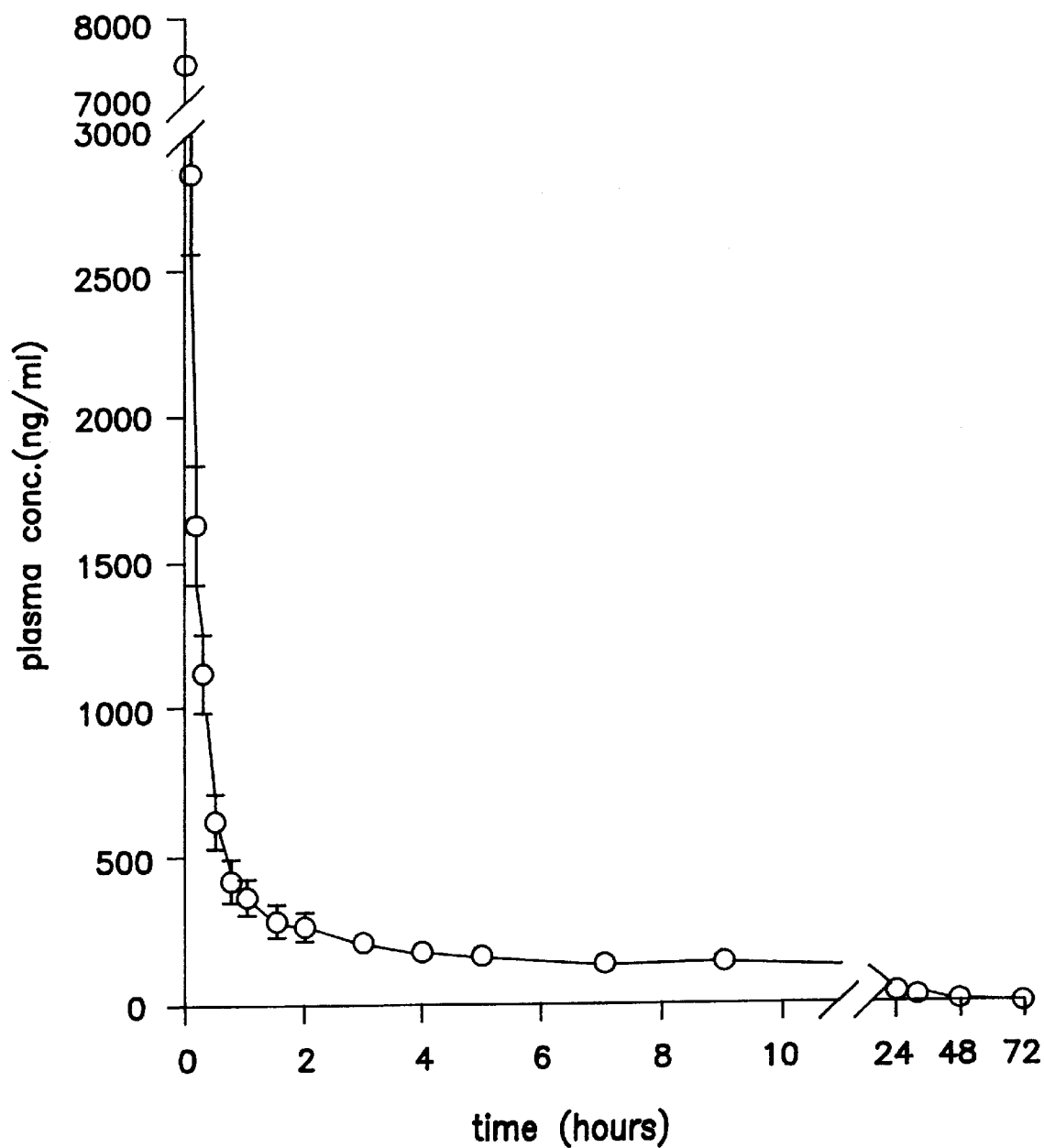
FIG. 1 presents the mean halofantrine plasma concentration-time profile after the intravenous administration of the halofantrine free base/Intralipid® to three fasted male beagle dogs.

The present invention therefore provides, in a first aspect, halofantrine in the form of its free base ('halofantrine free base') for use in parenteral or oral therapy, in particular in the treatment of malarial infection.

Suitable formulations for parental use include injectable formulations for administration via intravenous (i.v.) and intramuscular (i.m.) injection.

In particular, the injectable formulations provided herein are lipid based formulations of halofantrine free base. For example, a lipid based formulation for i.v. administration can be prepared in-situ using Intralipid® where the halofantrine free base is incorporated in the internal lipid phase of the commercially available i.v. emulsion as hereinafter described. More preferably, lipid-based emulsions suitable for i.v. administration can be prepared de novo where halofantrine free base is initially incorporated in the internal lipid phase which is then emulsified in a suitable external phase.

Other suitable lipid based-vehicles include, for example, emulsions prepared from short, medium or long chain triglycerides (or diglycerides or fatty acid derivatives) such as soybean oil which have been emulsified with either a synthetic or natural emulsifier (e.g. lecithin). In addition, such compositions may also contain a surfactant such as Tween 80.

For intramuscular administration, a formulation can be prepared using a water immiscible solvent such as medium or long chain triglycerides, benzyl benzoate (or combinations thereof) or other such solvents where the free base form of halofantrine is dissolved/dispersed in a biocompatible injectable vehicle.

In a still further aspect, the present invention also relates to oral formulations of halofantrine free base. More particularly, the formulations are either liquid or semi-solid formulations of the free base which will be administered as either a soft gelatin or hard gelatin capsule formulation. Such formulations can be prepared using standard techniques and in particular include dispersed lipid formulations, self emulsifying formulations, microemulsions and dispersable solid formulations. In particular, dispersed lipid formulations may be prepared by dissolving the free base in an appropriate lipid vehicle which may, or may not, include either a synthetic or natural surfactant which would promote emulsification of the formulation after oral administration. Triglycerides, diglycerides, monoglycerides, fatty acids or derivatives of fatty acids, monoglycerides, diglycerides or triglycerides, are acceptable vehicles. Long chain fatty acids, medium chain and short chain fatty acids are suitable with long and medium chain fatty acids or triglycerides thereof being particularly preferred. More specifically, preferred formulations are those comprising halofantrine free base, a medium/long chain triglyceride lipid, a medium/long chain mono diglyceride lipid and a surfactant.

Suitable medium chain mono/diglyceride lipids include Capmul MCM (mono and diglycerides of medium chain fatty acids (caprylic and capric acids), available from Karlshamns Lipids, Columbus, Ohio, USA). Suitable long chain mono/diglyceride lipids include Maisine 35-1 (mono and diglycerides of long chain fatty acids from maize oil, available from Gattefosse s.a., France).

Suitable medium-chain triglycerides include Miglyol 810 (triglyceride of fractionated coconut oil ($C_8$ caprylic acid, and $C_{10}$ capric acid)); Miglyol 812 (triglyceride of fractionated coconut oil ($C_8$–$C_{10}$ fatty acids)); Miglyol 818 (triglyceride of fractionated coconut oil ($C_8$–$C_{10}$ fatty acids) with a 5% portion of linoleic acid)); Captex 300 (triglyceride of caprylic/capric acid ($C_8$–$C_{10}$) fatty acids)); Captex 350 (triglyceride of fractionated coconut oil containing $C_8$–$C_{10}$–$C_2$ fatty acids) and Captex 355 (triglyceride of caprylic/capric acid ($C_8$–$C_{10}$ fatty acids)). Suitable long chain triglycerides include peanut oil, safflower oil and soya bean oil; other suitable long chain triglycerides will be apparent to those skilled in the art.

Suitable liquid self emulsifying/dispersing formulations include, for example, halofantrine free base dissolved in a suitable vehicle such as peanut oil or Captex 355 and one or more dispersing agents/surfactants such as a polyglycolyzed glycerides, propylene glycol esters, glycerol esters, polyethoxylated glycerol derivatives, sorbitan ester derivatives, polyoxyethylene sorbitan ester derivatives and other suitable dispersing/surfactant agents known to those skilled in the art.

More reliable or readily absorbed formulations allow manipulations of both dose per unit of formulation and dosing frequency for acute therapy in order to attain adequate therapeutic plasma concentrations of halofantrine.

Suitable semi-solid self emulsifying/dispersing formulations include for example halofantrine free base dissolved in a solid/semi-solid matrix which either disperses or forms a microemulsion/micellar system upon contact with an aqueous environment.

Semi-solid or solid formulations containing the free base can be prepared by incorporating the melted free base (initially prepared as either an amorphous or crystalline form) with appropriate excipients which either disperse or form a micellar solution upon contact with water. This approach has the advantage of achieving high drug loadings per unit dose and the semi-solid/solid nature of the formulation limits potential physical changes that can occur in liquid based formulations. Furthermore, such formulations can be filled into either hard or soft gelatin capsules.

Representative matrices suitable for preparing semi-solid/solid systems include, but are not limited to, polyethylene glycol 6000 (PEG 6000), a Gelucire® pharmaceutical excipient (such as Gelucire 44/14 which is a hydrogenated food-grade oil containing $C_8$–$C_{18}$ glycerides and $C_8$–$C_{18}$ ethoxylated fatty acids available from Gattefosse S.A., 36 Chemin de Genas, F-69800, Saint Preist, France), or Vitamin E TPGS (d-α-tocopheryl polyethylene glycol 1000 succinate available from Eastman Chemicals, Kingsport, Tenn., USA) or combinations thereof. These systems may also include additional agents such as surfactants/dispersants and standard formulation excipients such as silicon dioxide, lactose and starch and polvinylpyrrolidone.

Alternative formulations for oral use will be apparent to those skilled in the art and include, for example, solubilized formulations prepared using a surfactant/co-solvent mixture, spray dried solid formulations where the free base has been dissolved in a solvent and then spray dried onto a solid carrier system, matrix based formulations where the matrix system slowly dissolves/erodes thereby slowly releasing the free base form of halofantrine.

The following data and examples serve to illustrate the invention. The solubility of halofantrine hydrochloride in a triglyceride lipid such as peanut oil is less than 1 mg/ml, whereas crystalline in halofantrine free base is soluble in triglycerides at concentrations in excess of 80 mg/ml, and the amorphous form of the base is miscible/soluble with peanut oil at concentrations in excess of 400 mg/ml. (For comparative purposes, the solubility of halofantrine hydrochloride in aqueous solutions is approximately 1 μg/ml).

Preparation of Crystalline Halofantrine (Hf) Base 4.3 g of Hf.HCl (equivalent to 4 g free base) was dissolved in 200 ml of 100% ethanol. The ethanolic solution was then vigorously stirred with a magnetic stirrer while 10 ml of a 1 M NaOH solution (1.2 molar equivalents of Hf) was slowly added. The solution was stirred for a further 10 minutes after which seed crystals of crystalline base and 10 ml of Milli-Q water were slowly added. The solution was left stirring overnight, after which the precipitate was filtered (Whatman #1 filter paper) and washed with 200 ml of ethanol/water (50:50). The solid was dried under vacuum over $P_2O_5$ at 60° C. for 24 hours. Yield was typically 75–80%, m.p. 81–84° C.

Techniques used to characterise solid Hf base include DSC (to determine onset of melting (typically 80–81° C.) and the enthalpy of fusion (typically 62–64 J/g), thermogravimetric analysis to quantitate the presence of any volatile solvents (dried until less than 0.5%), NMR, Mass spectrometry and HPLC to determine identity and purity.

Preparation of Amorphous Halofantrine (Hf) Base

Amorphous halofantrine free base was prepared from the crystalline material. 4g of crystalline Hf base was dissolved in approximately 150 ml of dry dichloromethane and filtered (Whatman #1 filter paper) into a 250 ml round bottom flask. The solvent was then evaporated on a rotary evaporator at 50–60° C. and the amorphous Hf base then dried under vacuum over $P_2O_5$ at 60° C. for 24 hours. Thermogravimetric analysis indicated less than 0.5% weight loss on heating from 30 to 200° C.

1. Intravenous Formulations

A. An intravenous preparation of halofantrine free base was prepared using a commercially available lipid emulsion (Intralipid® available from Baxter Healthcare). For example, thirty ml batches were prepared under aseptic conditions by the careful dropwise addition of an appropriate amount (approximately 500 μl) of a dimethylfcrmamide solution of halofantrine free base (120 mg/ml) to Intralipid®, whilst rapidly vortexing the emulsion in a clean silanized glass beaker. The emulsion was examined under a polarized light microscope to confirm the absence of any precipitated material.

B. The preparation of an emulsion containing halofantrine free base suitable for i.v. administration can also be accomplished by first dissolving halofantrine free base in an appropriate lipid phase and then preparing the emulsion. For example, halofantrine free base was prepared at a concentration of 40 mg Hf base per gm of soybean oil. 1.2 gram of egg phospholipids (available from Pfanstiehl Laboratories Inc, Ill., USA) were dispersed in approximately 70 ml of distilled water, after which 10 gram of soybean oil (containing the Hf base) was added, and the final mass of the formulation made to 100 gram by the addition of distilled water. A 'course' emulsion was first prepared using a high-shear Silverson laboratory mixer emulsifier (Silverson Machines Ltd, UK). This emulsion was then cycled through a Model 110-Y Microfluidizer (Microfluidics Corp, Mass., USA) operated at approximately 15,000 psi. A uniform emulsion (containing 4 mg Hf base per gram of emulsion) was produced with a final droplet size of approximately 250 nm as estimated by photon correlation spectroscopy. As necessary, the osmolarity of the emulsion is adjusted with an appropriate agent such as glycerol, and tile pH controlled. If necessary, the formulation of insoluble halofantrine HCl in the external phase can be prevented by control over the pH of the external phase or by the addition of a solubilizing surfactant to the external phase. The emulsion could be sterilized by either autoclaving or passage through a sterilizing filter. The concentration of Hf base within the emulsion can be optimised by altering tie proportion of oil within the emulsion between typical values of 1–25% w/w and drug concentrations between 0.1 and 10 mg/ml of emulsion.

FIG. 1 presents the mean halofantrine plasma concentration-time profile after the intravenous administration of the halofantrine free base/Intralipid® described in (A) above to three fasted male beagle dogs. The dose level of halofantrine was 1.6 mg/kg, and the plasma concentration of halofantrine was determined using a validated HPLC assay.

2. Oral Formulations The unexpectedly high lipid solubility and miscibility of halofantrine free base has enabled many different oral formulation approaches to be developed. For example, halofantrine free base can be formulated as a lipid solution, or as formulations which readily disperse upon contact with water.

2.1 Lipid Based Formulations

A number of different formulations of halofantrine free base were prepared and evaluated in bioavailability studies conducted in beagle dogs. As a point of reference, the reported absolute bioavailability (mean±SD, n=4) of 250 mg halofantrine hydrochloride tablets (HALFAN™), in fasted beagle dogs is 7.1+ 4.6% (Humberstone el al., Pharm. Res., 11, S-292, 1994).

For example, one relative bioavailability crossover study was undertaken which compared the following formulations: (i) a standard commercially available 250 mg Hf.HCl tablet (HALFAN™), (ii) a solution of Hf base in peanut oil (233 mg of the base dissolved in a total volume of 1 ml of peanut oil), (iii) a self-emulsifying drug delivery (SEDD) formulation comprising 233 mg Hf base, 400 mg peanut oil and 350 mg Tagat TO (Th. Goldschmidt AG, Essen, Germany) and, (iv) a self-emulsifying drug delivery (SEDD) formulation comprising 233 mg Hf base, 400 mg miglyol 812 and 350 mg Tagat TO. Tagat TO is a polyethoxylated castor oil derivative which provides for self-emulsification of the formulation and miglyol is a medium chain triglyceride. Standard surfactants (with GRAS status) could also be used for this purpose. Miglyol 812 is a standard medium chain triglyceride available from R. P. Scherer Pty. Ltd. All lipid formulation of the Hf free base were filled into oblong soft gelatin capsules (size 22 minims).

The bioavailability study was conducted as a four treatment, four period, randomized cross over study conducted in four male beagle dogs. The washout period between treatments was 10 days. Dogs were fasted for 12 hours prior to drug administration and for a subsequent 10 hour period post-drug administration, after which they were fed at 24 hour intervals. Water was available ad libitum.

Venous blood samples (2.5.ml) were taken, via an indwelling catheter in the cephalic vein, prior to medication (−15min) and 0.5, 1, 1.5, 2, 2.5, 3, 4, 6, 8, 10, 24, 28, 48, 72, 96, 120, 144 and 168 h post-medication after oral administration. Blood samples were collected in sterile tubes containing 4.5 mg dipotassium EDTA. Plasma was separated by centrifugation and stored frozen at −70° until analyzed. Plasma concentrations of halofantrine and desbutylhalofantrine (the major metabolite) were determined by a validated HPLC assay utilising UV detection (Humberstone and co-workers, J. Pharm. Biomed. Anal., in press, 1995).

Calculated pharmacokinetic parameters included the area under the plasma concentration time profile from time zero to infinity ($AUC^{0 \to \infty}$) as well as the maximum plasma concentration ($C_{max}$), and the time taken to reach $C_{max}$ ($t_{max}$). The AUC data were calculated using the linear trapezoidal rule to the last measured plasma concentration and adding to that the extrapolated area calculated by dividing the last measured plasma concentration by the terminal elimination rate constant.

Figure 2:
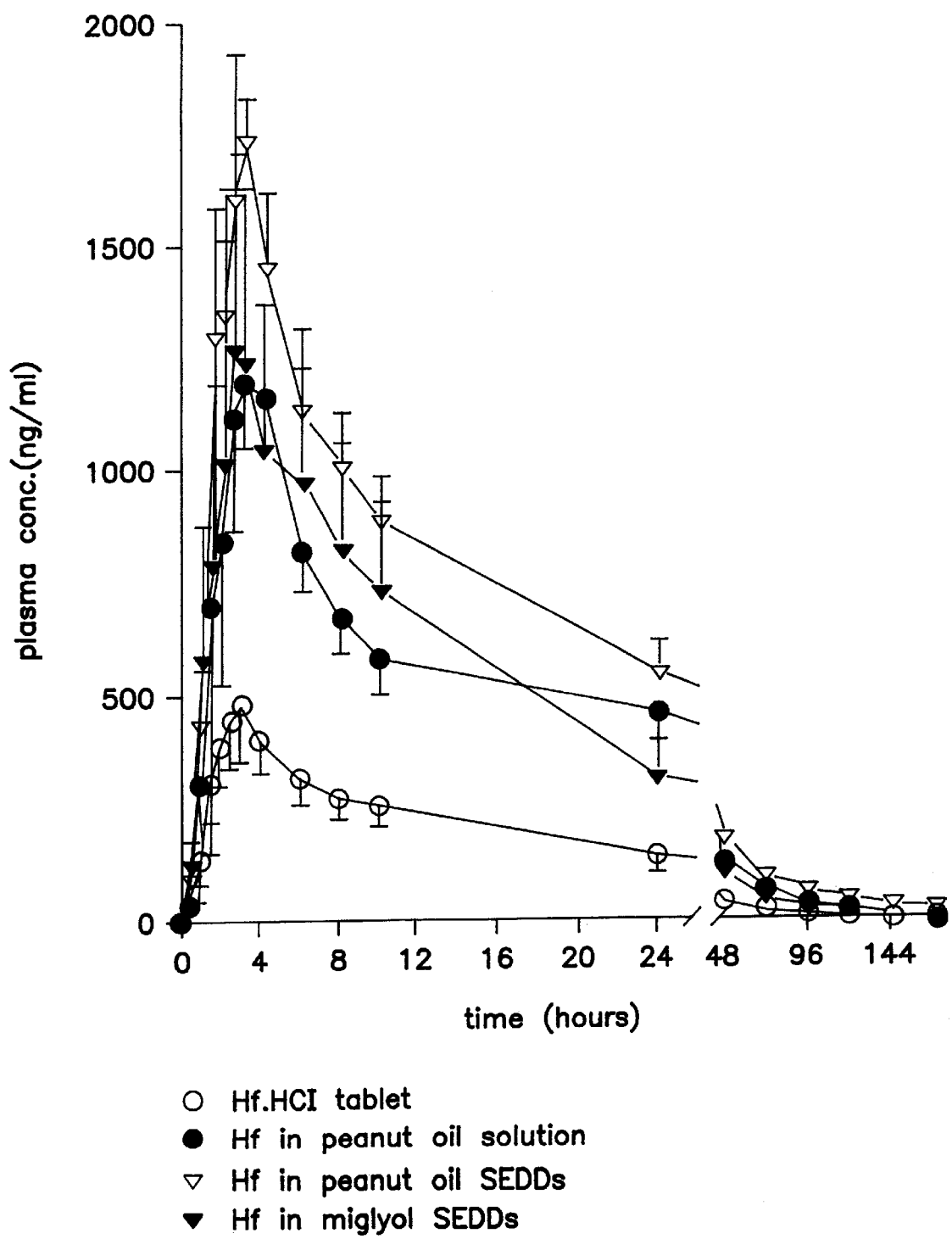
FIG. 2 presents the mean (+/−SD, n=4) halofantrine plasma concentration-time profile after the oral administration of these different formulations to four fasted male beagle dogs.

FIG. 2 presents the mean (±SD, n=4) Hf plasma concentration-time profile after the oral administration of these different formulations to four fasted male beagle dogs. The dose level was 233 mg Hf base.

Table 1 presents the summary pharmacokinetic parameters from this study (Mean±SD, n=4), and the average ratios of the AUC values from the Hf base formulations relative to the 250 mg Hf. HCl tablet.

TABLE 1

| Parameter | Hf.HCl tablet | Peanut oil solution | Miglyol SEDD | Peanut oil SEDD |
|---|---|---|---|---|
| $C_{max}$(ng/ml) | 487 ± 230 | 1467 ± 650 | 1399 ± 921 | 1950 ± 306 |
| $T_{max}$(h) | 2.9 ± 0.3 | 3.4 ± 1.3 | 3.7 ± 1.7 | 2.4 ± 0.7 |
| AUC ratio | — | 3.2 ± 0.9 | 3.2 ± 1.8 | 4.6 ± 1.6 |
| range of AUC ratios | | (2.2–4.6) | (0.4–4.3) | (2.8–6.2) |

2.2 Self-emulsifying Formulations

Three self-emulsifying systems were prepared from the following components:

Formulation A: Medium chain self emulsifying formulation (particle size 0.1–1μm)

| Composition (w/w) | Components | Working range (w/w) |
|---|---|---|
| 20.0% | Halofantrine base | 0–35% |
| 23.3% | Capmul MCM | 10–40% |
| 46.7% | Captex 355 | 20–85% |
| 10.0% | Tween 80 | 2–40% |

Formulation B: Medium chain self microemulsifying formulation (particle size: <40 nm)

| Composition (w/w) | Components | Working range (w/w) |
|---|---|---|
| 20.0% | Halofantrine base | 10–30% |
| 13.3% | Capmul MCM | 10–20% |
| 26.7% | Captex 355 | 20–40% |
| 40.0% | Tween 80 | 30–40% |

Formulation C: Long chain self emulsifying formulation (particle size: <1 μm)

| Composition (w/w) | Components | Working range (w/w) |
|---|---|---|
| 20.0% | Halofantrine base | 0–35% |
| 20.0% | Maisine | 10–50% |
| 40.0% | Peanut Oil | 20–80% |
| 20.0% | Tween 80 | 10–40% |

The particle size of formulations was determined upon 'dissolution analysis' of formulations A, B and C. The dissolution was conducted in a standard USP apparatus at 37° C. using 400 ml of 0.1 N HCl and paddle speed of 100 rpm. Typically, 300 μl of formulation was added to 400 ml of the dissolution medium and a sample was then taken for particle size analysis conducted using photon correlation spectroscopy.

The absolute oral bioavailbility of these three oral formulations was assessed in a further study conducted in fasted beagle dogs. The treatment legs were (i) a medium chain self emulsifying formulation (Formulation A above), (ii) a medium chain self microemulsifying formulation (Formulation B above), (iii) a long chain self emulsifying formulation (Formulation C above), and (iv) an intravenous formulation prepared as described in example 1 above.

The oral dose was 200 mg halofantrine free base per soft gel capsule, and each soft gel formulation was adminstered with approximately 80 ml of water. The i.v. dose of halofantrine base (3 mg/kg) was adminstered over a 15 minute period via an indwelling catheter in the cephalic vein.

Venous blood samples (2.5 ml) were taken, via an indwelling catheter in the cephalic vein, prior to medication (−15 min) and at 0 (end of infusion), 15, 30, 60 and 90 min, and 2, 3, 4, 6, 8, 10, 24 28, 32, 48, 72 and 96 h postmedication after i.v. administration; and at −10 min and 0.5, 1, 1.5, 2, 3, 4, 6, 8, 9, 10, 24, 48, 72 and 96 h post-medication after oral administration. Blood samples were collected in sterile tubes containing 4.5 mg dipotassium EDTA. Plasma was separated by centrifugation and stored forzen at −70° C. until analysed. Plasma concentrations of halofantrine and desbutylhalofantrine (the major metobolite) were determined by a validated HPLC assay utilizing UV detection (Humberstone and co-workers, J. Pharm. Biomed. Anal., in press, 1995).

Calculated pharmacokinetic parameters included the area under the plasma concentration time profile from −15min (start of infusion) to time infinity ($AUC^{15 \to \infty}$) after IV administration, and from time zero to infinity ($AUC^{0 \to \infty}$) for the oral administrations as well as the maximum plasma concentration ($C_{max}$), and the time taken to reach $C_{max}$ ($t_{max}$). The AUC data were calculated using the linear trapezoidal rule to the last measured plasma concentration and adding to that the extrapolated area calculated by dividing the last measured plasma concentration by the terminal elimination rate constant. The absolute bioavailability of halofantrine from the different oral formulations was calculated as the ratio of the dose normalised AUC values after oral and i.v. administration according to standard procedures.

Figure 3:
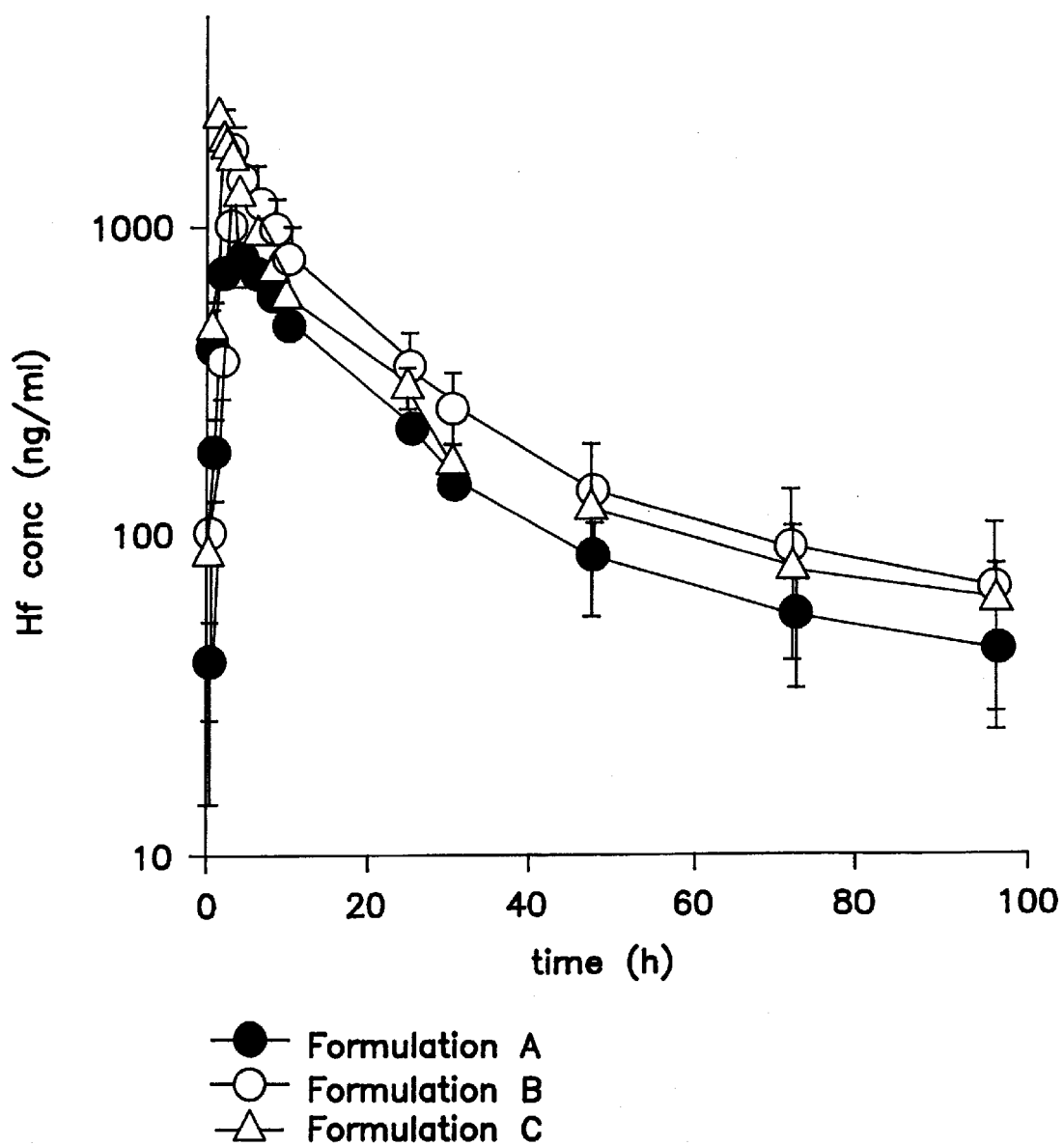
FIG. 3 depicts the mean plasma halofantrine concentration vs. time profiles after oral administration of the three prototype lipid-based formulations.

FIG. 3 depicts the mean plasma halofantrine concentration vs. time profiles after oral administration of the three prototype lipid-based formulations.

Table 2 presents pertinent pharmacokinetic parameters from the bioavailability study where the three oral formulations (each containing 200 mg halofantrine free base) were compared with an intravenous control formulation.

unit doses of formulated halofantrine free base will be able to achieve similar efficacy as the current 250 mg Hf.HCl tablet.

2.3 Semi-Solid Formulations

Semi-solid self emulsifying/dispersing formulations of halofantrine free base dissolved in a solid/semi-solid matrix have been prepared which either disperse or form a microemulsion/emulsion system upon contact with an aqueous environment.

Solid/semi-solid formulations of Hf base offer the advantages of higher drug loadings per unit formulation than can be achieved with homogeneous solutions, and this offers potential advantages in terms of dosing regimens and the number of formulation units per therapeutic dose. Furthermore, it is well known that the dissolution rate of semi-solid/solid formulations can be controlled by the inclusion of standard pharmaceutical excipients. This can translate into utilisation of formulation appraoches for controlling and optimising the Cmax and Tmax plasma values of Hf after administration of an oral semi-solid/solid formulation with a view to decreasing the Cmax value (which would probably lead to an increase in the Tmax value) which would be beneficial in lessening the potential for unwanted side effects of halofantrine due to excessively high Cmax values. The use of such formulations, and the means of achieving such modificiations to drug release rate, are well known in the art. For example, these appraoches are well described in the technical literature associated with the Gelucire product.

Typical formulations contain 20% halofantrine base (w/w) in up to 80% (w/w) of one of the matrices herinbefore described. The formulations were prepared by melting solid crystalline halofantrine base and then mixing with the selected matrix, or using amorphous halofantrine base and mixing with the selected matrix with the aid of gentle heating. The molten mass was then filled into either a hard or a soft gelatin capsule shell and rapidly cooled. Once solidified, the crystalline character of the final formulation was monitored using X-Ray Diffraction. These systems may also include additional agents such as surfactants/ dispersants as hereinbefore described and standard formulation excipients such as silicon dioxide, lactose and starch and polvinylpyrrolidone.

When the dispersion characteristics of these representative formulations which contained 200 mg of halofantrine base (in a 1 gram fill comprised of 80% w/w of either Gelucire 44/14 or Vitamin E TPGS) were assessed in standard USP dissolution apparatus (operation at a paddle rotation of 1000 rpm, 37° C. and using 400 ml 0.1 N HCl), a clear solution was produced within 30 minutes of intro-

TABLE 2

| Parameter<br>Mean ± SD (n = 4) | Formulation A<br>Medium chain self<br>emulsifying | Formulation B<br>Medium chain self<br>emulsifying | Formulation C<br>Long chain self<br>emulsifying |
| --- | --- | --- | --- |
| $C_{max}$(ng/ml) | 1018 ± 302 | 1856 ± 542 | 2567 ± 1074 |
| $T_{max}$(h) | 3.25 ± 1.0 | 2.4 ± 0.5 | 1.9 ± 0.8 |
| $AUC^{0 \to \infty}$(ng.h/ml) | 20289 ± 2658 | 33241 ± 13028 | 29828 ± 12765 |
| Absolute Bioavailability (%) | 39.7 ± 6.6 | 63.9 ± 19.9 | 57.1 ± 19.6 |

Based on the greater absorption of Hf available from these lipid-based formulations which contain halofantrine free base, relative to the commercial HALFAN® tablet which contains halofantrine hydrochloride where the absolute bioavailability in fasted dogs is 7.1 ±4.6%, it is likely that lower duction of the capsule into the dissolution apparatus. The particle size of the dispersed phase was approximately 30–100 nm as estimated by photon correlation spectroscopy. These formulations, which are able to completely solubilise the formulated Hf base upon introduction into the dissolution apparatus and produce a clear 'micellar' solution with an estimated particle size of 30–100 nm, are physically and functionally similar to the previously described Formulation B (medium chain selfmicroemulsifying formulation) which afforded high absolute oral bioavailability of Hf. Such semi-solid formulations would therefore be expected to afford high drug bioavailability after oral adminstration.

We claim:

1. A pharmaceutical formulation comprising halofantrine free base in association with a pharmaceutically acceptable carrier in a form suitable for oral administration in which the formulation is a self-emulsifying formulation.

2. A formulation according to claim 1 comprising halofantrine free base, a medium/long chain triglyceride lipid, a medium/long chain mono/diglyceride lipid and a surfactant.

3. A pharmaceutical formulation according to claim 2 in which the medium chain trigyceride lipid is a triglyceride of a $C_{8-10}$ fatty acid; the medium chain mono/diglyceride is a mono/diglyceride of caprylic or capric acid; and the surfactant is polyoxyethyelene 20 sorbitan monoleate.

4. A pharmaceutical formulation according to claim 2 in which the long chain triglyceride lipid is peanut oil, the long chain mono/diglyceride is a mono/diglyceride of a long chain fatty acid from maize oil, and the surfactant is polyoxyethyelene 20 sorbitan monoleate.

5. A formulation according to claim 1 in which the formulation is a semi-solid/solid formulation which either disperses or forms a microemulsion/micellar system upon contact with aqueous environment.

6. A pharmaceutical formulation according to claim 5 in which the matrix used to prepare the semi solid/solid formulation is selected from polyethylene glycol 6000, a hydrogentated food-grade oil containing $C_{8-18}$ glycerides or $C_{8-18}$ ethoxylated fatty acids, and d-α-tocopheryl polyethylene glycol 100 succinate and combinations thereof.

7. A formulation according to claim 6 further comprising an ingredient selected from the group consisting of a surfactant/dispersant, silicon dioxide, a filler, a disintegrant, and an excipient, wherein the ingredient is used to modify the rate of drug release from the formulation.

8. A pharmaceutical formulation comprising halofantrine free base and a pharmaceutically acceptable carrier in a form suitable for intravenous administration.

* * * * *